United States Patent [19]

Deguchi et al.

[11] 4,149,892
[45] Apr. 17, 1979

[54] COLOR DIFFUSION TRANSFER PHOTOGRAPHIC ELEMENTS

[75] Inventors: Hidetaka Deguchi, Tama; Jiro Takahashi, Hachioji; Naoshi Kunieda, Tokyo, all of Japan

[73] Assignee: Konishiroku Photo Industry Co., Ltd., Tokyo, Japan

[21] Appl. No.: 810,910

[22] Filed: Jun. 29, 1977

[30] Foreign Application Priority Data

Jul. 1, 1976 [JP] Japan .................................. 51-78057

[51] Int. Cl.² .......................... G03C 1/40; G03C 5/54; G03C 1/10
[52] U.S. Cl. .................................. 96/77; 96/29 D;99
[58] Field of Search ....................... 96/3, 29 D, 77, 99, 96/51

[56] References Cited

U.S. PATENT DOCUMENTS

B 351,673  1/1975  Fleckenstein et al. .............. 96/29 D

OTHER PUBLICATIONS

"Photographic Systems" Fleckenstein, Research Disclosure, No. 13024 2/1976.

Primary Examiner—Richard L. Schilling
Attorney, Agent, or Firm—Bierman & Bierman

[57] ABSTRACT

A novel color diffusion transfer photographic element is disclosed which is characterized as having a photosensitive element containing a compound represented by the formula

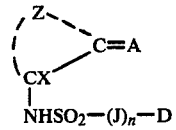

wherein A represents oxygen or a group of the formula =NR (in which R represents hydroxyl or an amino group); X represents hydrogen or halogen; Z represents a group of nonmetallic atoms necessary to form a first ring and being a 5 to 7-membered nonaromatic hydrocarbon ring which may be fused with a second ring, at least one of said first ring and said second ring having one or more substituents wherein at least one of said substituents is a ballast group which renders said compound nondiffusible during processing with said solution; J represents a divalent group; D represents a dye moiety or a dye precursor moiety; and n represents zero or 1.

18 Claims, No Drawings

COLOR DIFFUSION TRANSFER PHOTOGRAPHIC ELEMENTS

BACKGROUND OF THE INVENTION

This invention relates to a color diffusion transfer photographic element. Particularly, the invention is concerned with a color diffusion transfer photographic element comprising a novel color image forming material.

As for a color diffusion transfer process by use of a color diffusion transfer photographic element, there are various methods depending on the manner in which a color image forming material releases diffusible dyes when developing silver halide. A typical example of a first type method is the so-called dye developer method wherein a dye developer is a compound having both a dye moiety and a silver halide developing moiety in one molecule and the dye developer as a color image forming material is oxidized with silver halide so as to change its diffusibility.

This type method for a color diffusion transfer process is disclosed in many patents such as British Pat. No. 804,971.

In the above-mentioned dye developer method, a dye developer generally in an unexposed area after imagewise exposure of a photographic element is diffusion-transferred to an image receiving layer and the transferred dye developer still has a silver halide developing moiety which is quite reactive. Consequently, it adversely affects on the dye image obtained which image suffers from color stain or change in color tone due to air oxidation or the like reaction since the transferred dye developer is reactive as mentioned above.

A typical example of a second type method is the method using, as a color image forming material, a silver halide color developer which is oxidized by silver halide and subjected to a coupling reaction with a nondiffusible color image forming material and, further in some cases, subjected to a ring closure reaction to release diffusible dyes.

This type method for a color diffusion transfer process is disclosed, for example, in U.S. Pat. Nos. 3,227,550, 3,443,940 and 3,227,551, and British Patent 904,365.

In the above-mentioned second type method, it is essential to use a silver halide color developer which usually is a p-phenylenediamine type compound.

In many cases, the above-mentioned p-phenylenediamine type compound gives unfavorable effects to dye images because its oxidation product generally causes serious color stains. Further, said p-phenylenediamine type compound has a tendency to cause dermatitis on the skin of users in practical use.

In addition to the above-mentioned two type methods, there is a third type method, of which typical example uses nondiffusible color image forming materials either directly oxidized by silver halide or subjected to an oxidation-reduction reaction with a silver halide developer oxidized by silver halide for causing a ring closure reaction or alkaline hydrolysis to release diffusible dyes or their precursors. (These materials are the so-called dye releasing redox compounds and hereafter they are called as the DRR compound.)

This type method for a color diffusion transfer process is disclosed, for example, in U.S. Pat. Nos. 3,698,897, 3,725,062, 3,728,113, 3,245,789, 3,443,939 and 3,705,035, Japanese Laid-Open-to-Public Patent Publication Nos. 33,826/73, 118,723/75, 2,327/72 and 64,436/74, and Japanese Pat. Publication No. 39,165/73.

The above-mentioned third type method is advantageous, in comparison with the foregoing two type methods, in that what is transferred to an image receiving layer comprises only a dye moiety or a dye precursor moiety without any developing moiety as well as in that it is not essential to use a color developing agent such as p-phenylenediamine type compounds but possible to use a black-and-white silver halide developing agent and therefore dye images with reduced color stain may be obtained therein.

In the above-mentioned third type method; that is, the so-called DRR method, a photographic element containing a light sensitive silver halide emulsion layer and a nondiffusible color image forming material; that is, the DRR compound, is exposed to the irradiation to form a latent image in light sensitive silver halide, and then, if desired, treated with an alkaline processing solution in the presence of a silver halide developing agent. At the time of the treatment with the alkaline processing solution, the above-mentioned photographic element and the image receiving element are superposed on each other and, as the result of the treatment, diffusible dyes released from the nondiffusible DRR compounds are transferred by diffusion to the image receiving layer, thereby to form dye images thereon.

The suitable compound used in the above-mentioned DRR method has to meet the following essential requirements:

(a) that it should be sufficiently stable before and after the processing;

(b) that it should react rapidly in an exposed area and should rapidly release diffusible dyes or their precursors at the time of processing; and (c) that it is sufficiently stable in an unexposed area even at the time of processing.

As the DRR compound used in the DRR method, there are known heretofore various compounds as disclosed in the above-mentioned patents.

It cannot be said, however, that any of the conventionally known DRR compounds satisfy all the above requirements of (a) to (c).

Thus, the object of the present invention lies in providing a novel color diffusion transfer photographic element comprising a novel color image forming material. Particularly, this invention resides in providing a novel color diffusion transfer photographic element suitable for a DRR method using a novel DRR compound. In other words, the object of the invention is more preferably to provide a novel color diffusion transfer photographic element for a DRR method using a novel DRR compound fully satisfying all the above-mentioned requirements of (a) to (c) which the DRR compound should meet. The still other object of the invention is to provide a new color diffusion transfer process according to a DRR method using a novel DRR compound which is sufficiently stable not only in case of the incorporation into an photographic element for the color diffusion transfer method but also in case of the preservation over a long period of time, and shows such a rapid reaction at the time of the exposure to the irradiation and of the subsequent treatment with an alkaline processing solution as to release diffusible dyes or their precursors.

Another object of this invention lies in preparing a color diffusion transfer image having little color stain but a clear and stable color tone within a shorter time according to said color diffusion transfer process.

SUMMARY OF THE INVENTION

The above-mentioned objects of the invention and any other objects which would be easily understood in the following description can be accomplished by a color diffusion transfer process characterized in imagewise exposing a photographic element comprising at least one light sensitive silver halide emulsion layer and a nondiffusible compound of the following general formula (I):

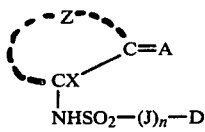

(wherein A represents oxygen or a group of the formula =NR (in which R represents hydroxyl or an amino group which includes substituted amino); X represents hydrogen or halogen; Z represents a nonmetallic atom group necessary to form a 5 to 7-membered nonaromatic hydrocarbon ring which may be fused with another ring, the 5 to 7-membered nonaromatic hydrocarbon ring and/or the another ring having one or more substituents at least one of which is a group to make the compound of the above-mentioned general formula (I) nondiffusible during a development with an alkaline processing solution; J represents a divalent group; D represents a dye moiety or a dye precursor moiety; and n represents zero or 1), developling said exposed photographic element with an alkaline processing solution in the presence of a silver halide developing agent to let said compound release diffusible dyes or their precursors, and subjecting said diffusible dyes or their precursors to diffusion transfer to an image receiving layer.

In the above formula, a $>C=N-R$ portion is prepared by subjecting a carbonyl reagent of $H_2N-R$ to the dehydration reaction with a ketone group when A is a group of $=NR$. The compound of $H_2N-R$ used in this case may include, for example, hydroxylamine, hydrazine, semicarbazide, and thiosemicarbazide compounds and the like. More particularly, said hydrazine compound may be, in addition to hydrazine, phenylhydrazine, substituted phenylhydrazine having at its phenyl group such substituent as an aryl group, an alkoxy group, a carboalkoxy group or halogen, and isonicotinic acid hydrazide. The semicarbazide compound may include phenylsemicarbazide, substituted pheylsemicarbazide having such substituent as an alkyl group, an alkoxy group, a carboalkoxy group or halogen. The thiosemicarbazide compound may include various derivatives of semicarbazide.

The typical examples of the 5 to 7-membered ring for Z may include, for example, cyclopentanone, cyclohexanone, cyclohexenone, cyclopentenone, cycloheptanone and cycloheptenone.

This 5 to 7-membered nonaromatic hydrocarbon ring may be also fused, at its suitable positions, with another ring to form a condensed ring. Herein, the another ring may include various rings whether or not it has aromaticity and whether it is a hydrocarbon ring or a heterocyclic ring.

Among such condensed rings, however, preferred are 5 to 7-membered nonaromatic hydrocarbon rings fused with benzene, such as indanone, benzocyclohexenone or benzocycloheptenone.

The 5 to 7-membered nonaromatic hydrocarbon ring and/or the condensed ring has one or more substituents selected from those substituents including an alkyl group, an aryl group, an alkyloxy group, an aryloxy group, an alkylcarbonyl group, an arylcarbonyl group, an alkylsulfonyl group, an arylsulfonyl group, a halogen atom, a nitro group, an amino group, an alkylamino group, an arylamino group, an amido group such as an alkylamido group and an arylamido group, an sulfamido, a cyano group, an alkylthio group, and an alkyloxycarbonyl group. The sulfamido in the above substituents may be $-NHSO_2-(J)_n-D$ (wherein J, D and n are as described before). In this case, the nonaromatic hydrocarbon ring may also additionally have such sulfamido group on the carbon atom adjacent to its carbonyl or $>C=N-R$ group.

X represents hydrogen or halogen such as fluorine, chlorine, bromine or the like and preferably hydrogen.

Among the substituents in Z, at least one is an organic group which makes the compounds of the above-mentioned general formula (I) nondiffusible in a photographic element during development with an alkaline processing solution, which group will be described below in detail. The typical examples of said group may include a long chain alkyl group, a benzene type or naphthalene type aromatic group and a long chain alkyl, benzene type or naphthalene type aromatic group bonded with one end of a suitable divalent group. The suitable divalent group herein is one member or any linear combination of two or more members belonging to the group consisting of —O—, —S—,

—SO₂—, —SO—,

—CR₂R₃—, —CR₂=CR₃— (in the above three formulae, R₁ represents hydrogen, an alkyl group or an aryl group; and R₂ and R₃ individually represent hydrogen, halogen, an alkyl group or an aryl group), a substituted or unsubstituted aromatic divalent group, and

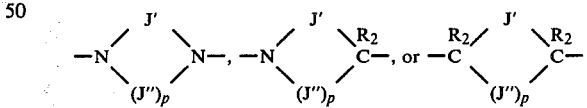

(in the above respective formulae: J' and J" individually represent a divalent group being one member selected from, or any combination of 2-4 members belonging to, the group consisting of —O—, —S—,

—SO₂—, —SO— and the beforementioned group

—CR$_2$R$_3$— and —CR$_2$=CR$_3$—; p represents 0 or 1; and J' and (J'')$_p$ form a 5 to 6-membered ring together with the N and/or C). The more preferred examples may include a substituted or unsubstituted C$_{8-22}$-alkyl group, or such group as a C$_{8-22}$-alkyl group (which includes substituted alkyl such as alkyloxy alkyl) or an aryl group (which includes substituted aryl such as alkyl or alkyloxy aryl) bonded with the terminal end of a divalent group being one member selected from, or any linear combination of two or more members belonging to, the group consisting of

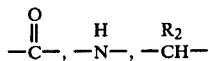

(wherein R$_2$ represents the same as described above), —O—, —SO$_2$— and a phenylene group.

In the above general formula (I), J represents a divalent group and n represents 0 or 1. The preferable group as represented by J in this invention is such divalent group as one member selected from or any linear combination of two or more members belonging to, the group consisting of —O—, —S—,

—SO$_2$—, —SO—,

—CR$_2$R$_3$—, —CR$_2$=CR$_3$— (in the above formulae, R$_1$ represents hydrogen, an alkyl group or an aromatic hydrocarbon group; and R$_2$ and R$_3$ individually represent hydrogen, halogen, an alkyl group or an aromatic hydrocarbon group), a substituted or unsubstituted aromatic divalent group, and,

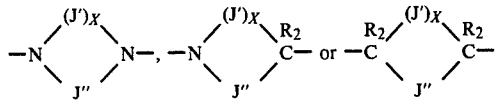

(wherein, J' and J'' individually represent a divalent group being one member selected from, or any combination of 2 to 4 members belonging to, the group consisting of —O—, —S—,

—SO$_2$—, —SO— and the above-mentioned groups

—CR$_2$CR$_3$— and —CR$_2$=CR$_3$—; X represents zero or 1; and (J')$_X$ and J'' together with N and/or C form a 5 to 6-membered ring as a whole).

The more preferable examples represented by J in this invention is those having the formula:

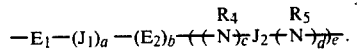

In the formula, E$_1$ and E$_2$ individually represent, a C$_{1-8}$-alkylene group or a phenylene group, while said alkylene or phenylene group includes those substituted with halogen or an alkyl or aryl group; R$_4$ and R$_5$ individually represent hydrogen, a C$_{1-8}$-alkyl group or a C$_{6-13}$-aryl group such as a phenylene group, a tolylene group or a naphthylene group; J$_1$ represents —O—,

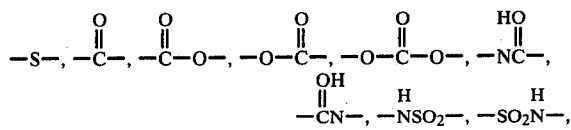

—SO—, —SO$_2$—, a C$_{1-8}$-alkylene group which includes alkylene substituted with halogen, a phenylene group or a substituted phenylene group; J$_2$ represents —SO$_2$—, or

a and b individually represent 0 or 1, but, when a is 1, b is 1 and when a is zero, b is rezo or 1 and when b is 1, the total number of carbon atoms of E$_1$ and E$_2$ is equal to or less than 14; and, c, d and e individually represent zero or 1 but the total of c and d is 1.

D represents a dye moiety or a dye precursor moiety. In the dye moiety as referred to herein, there may be included all those which are known to the art, such as an azo dye residue, an azomethine dye residue, an indoaniline dye residue, an indophenol dye residue, an anthraquinone dye residue, an azopyrazolone dye residue, an alizarin dye residue, a merocyanine dye residue, a cyanine dye residue, an indigoid dye residue and a phthalocyanine dye residue.

In the dye precursor moiety, there may be included a leuco dye residue (e.g. a leuco dye residue in a dye developing agent as disclosed in Japanese Laid-Open-to-Public Patent Publication No. 66,440/73), a shift type dye residue (a dye of which absorption shifts to shorter or longer wavelength region at the time of the alkaline processing, such as an acyloxynaphthyl azo dye residue, or a dye of which absorption shifts to shorter or longer wavelength region when fixed onto an image receiving layer as disclosed in Japanese Patent Application No. 78428/76) and a coupler component (e.g. phenol, naphthol, indazoline, pivalylacetoanilide, benzoylacetoanilide or pyrazolone). In this invention, when the dye precursor moiety is employed as D in the above-mentioned general formula (I), it is advantageous to incorporate thereinto an oxidizing agent, a color developing agent or a diazonium compound in order to transform diffusible dye precursors into dyes. As the image receiving element containing an oxidizing agent, a color developing agent or a diazonium compound as described above, there may be used such as disclosed in U.S. Pat. Nos. 2,647,049, 3,676,124 and 2,698,798, Japanese Laid-Open-to-Public Patent Publication No. 80,131/75 and French Patents 2,232,776 and 2,232,777. As disclosed therein, an oxidizing agent may be kept present in such alkaline processing solution as described later. Furthermore, such arts as disclosed in U.S. Pat. Nos. 2,774,668, 2,661,298 and 2,559,648 and British Pat. Nos. 1,157,501 and 1,157,510 may be used.

The typical examples of the compounds of the above general formula (I) which may be advantageously used in this invention are illustrated in the following but the said compound should not be limited only to these examples:

| Compound | |
|---|---|
| (1) | 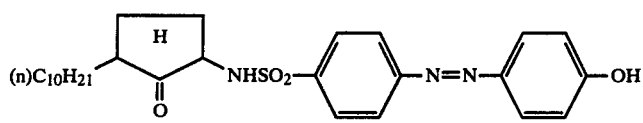 |
| (2) | 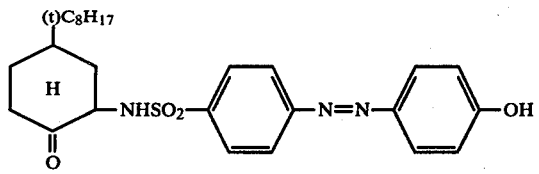 |
| (3) | 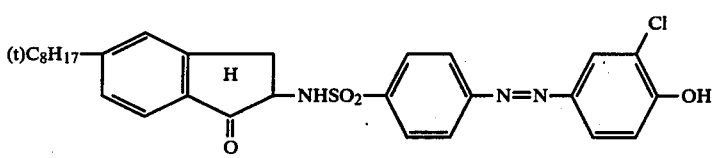 |
| (4) | 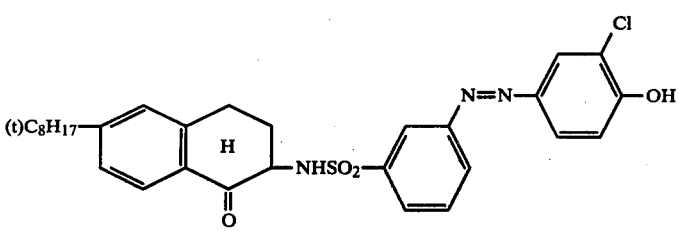 |
| (5) | 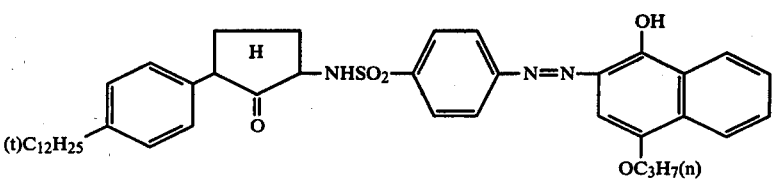 |
| (6) | 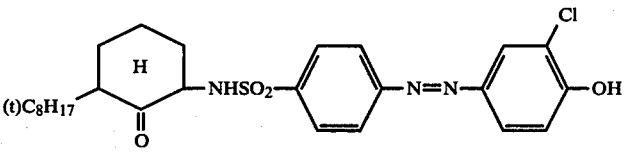 |
| (7) | 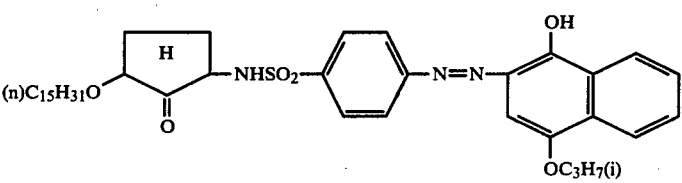 |
| (8) | 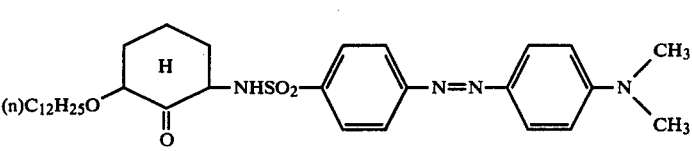 |
| (9) | 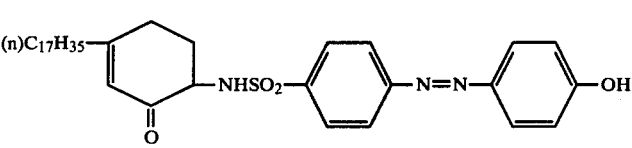 |
| (10) | 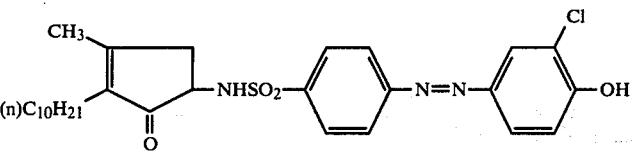 |

-continued
Compound
(11) 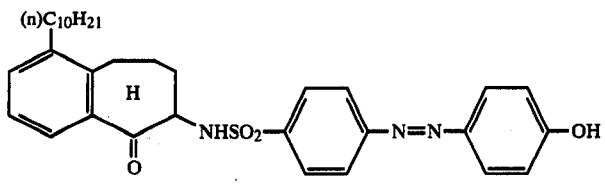
(12) 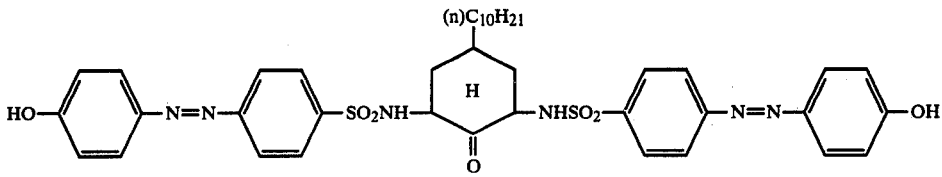
(13) 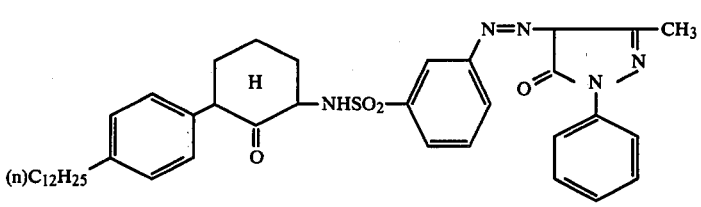
(14) 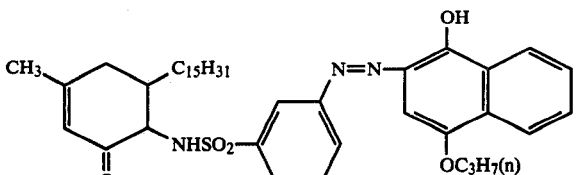
(15) 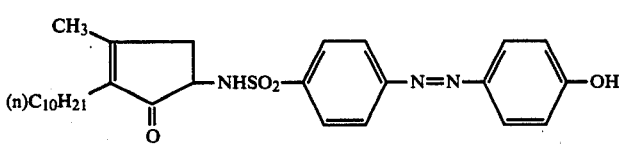
(16) 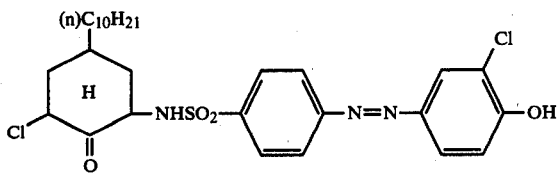
(17) 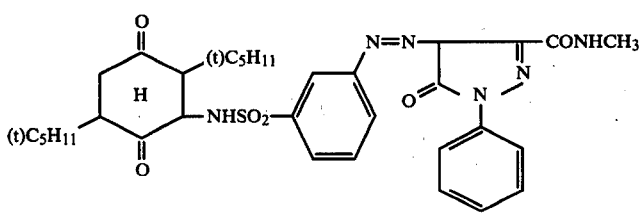
(18) 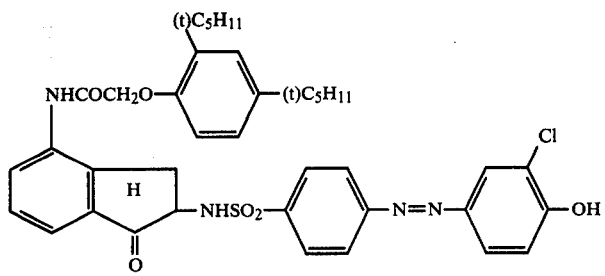
(19) 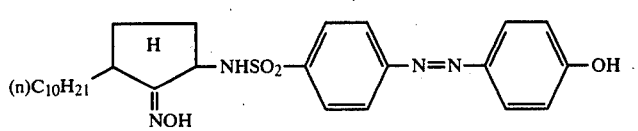

Compound
(20) 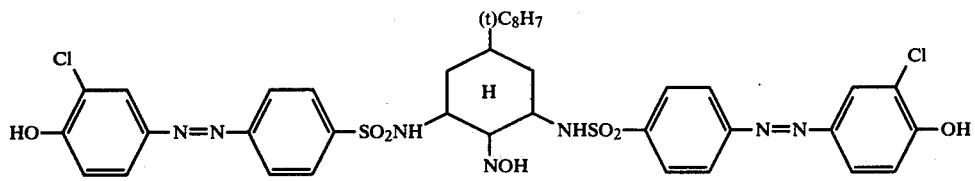
(21) 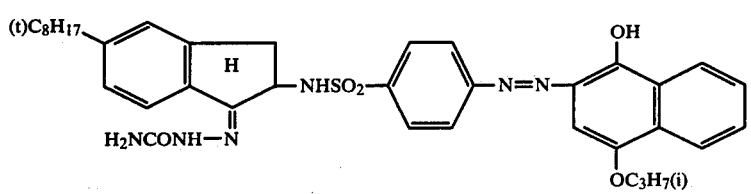
(22) 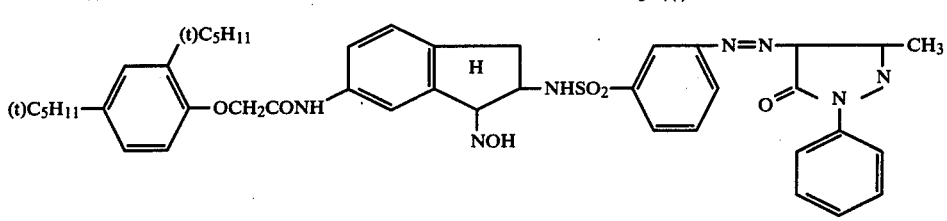
(23) 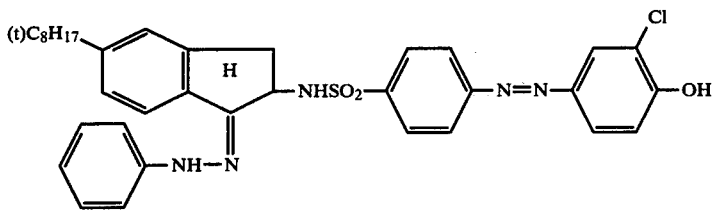
(24) 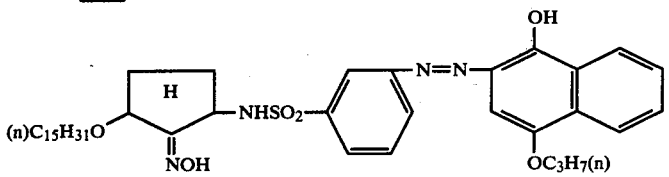
(25) 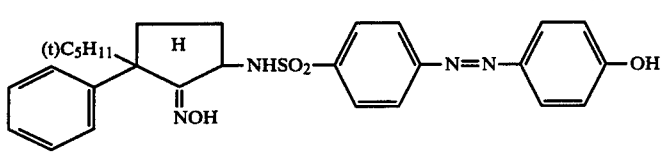
(26) 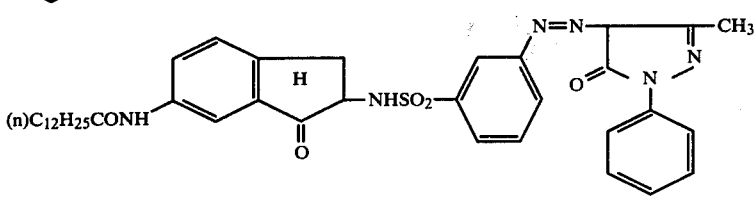
(27) 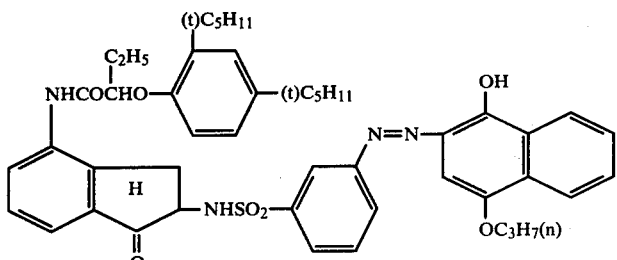
(28) 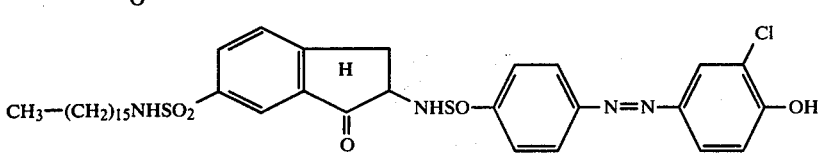

-continued
Compound
(29) 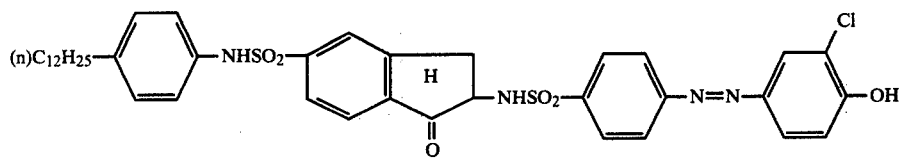
(30) 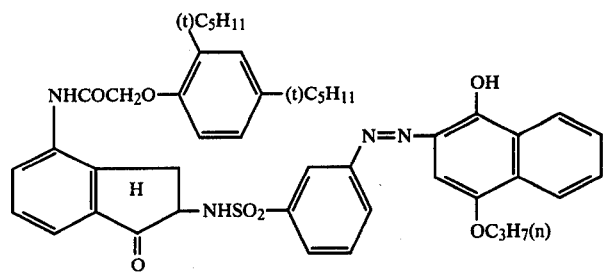
(31) 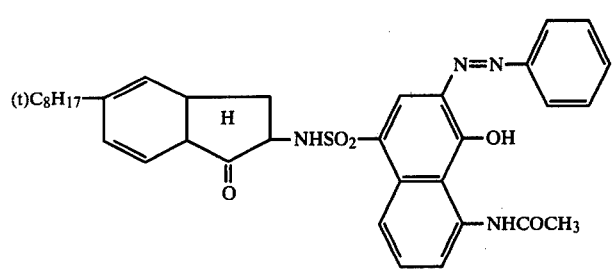
(32) 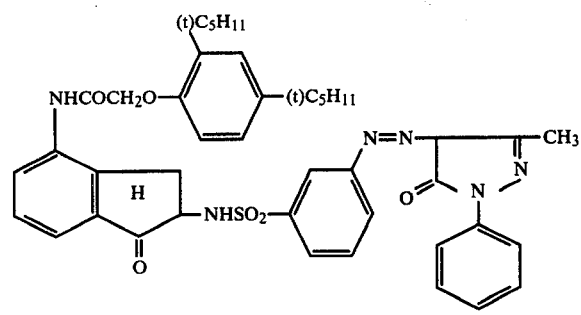
(33) 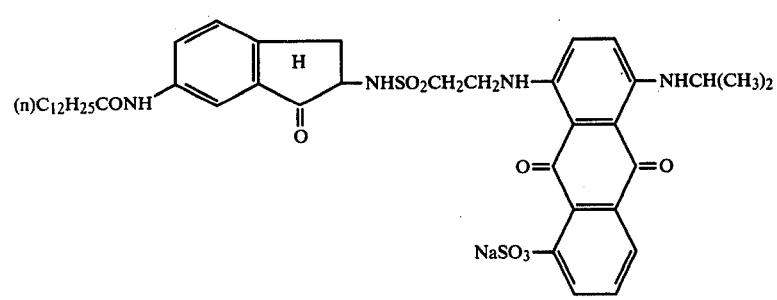
(34) 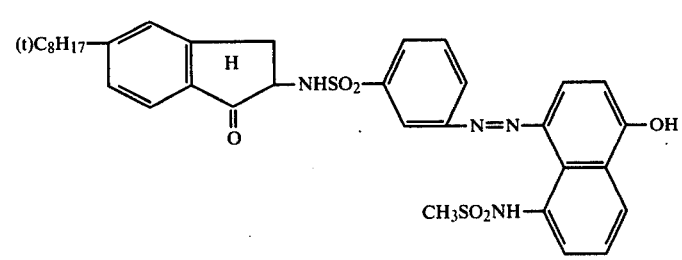

-continued
Compound
(35)
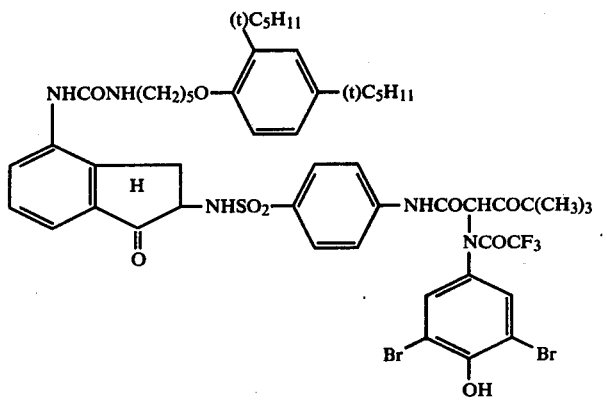
(36)
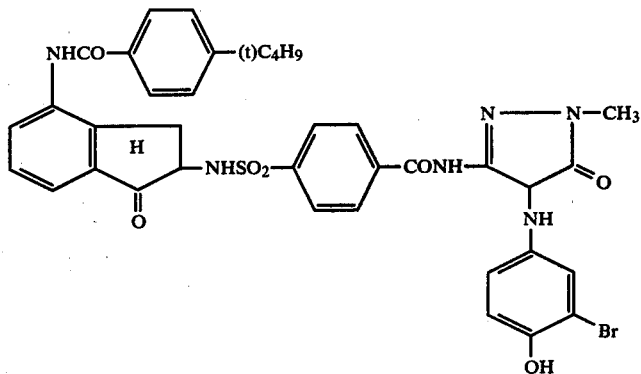
(37)
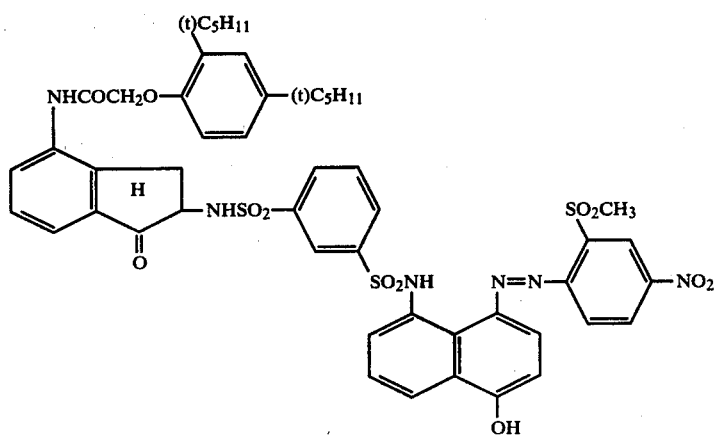
(38)
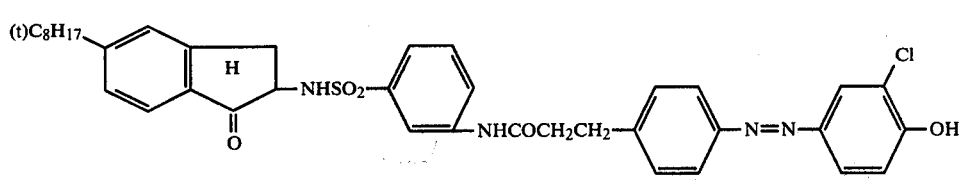

| Compound | |
|---|---|
| (39) | 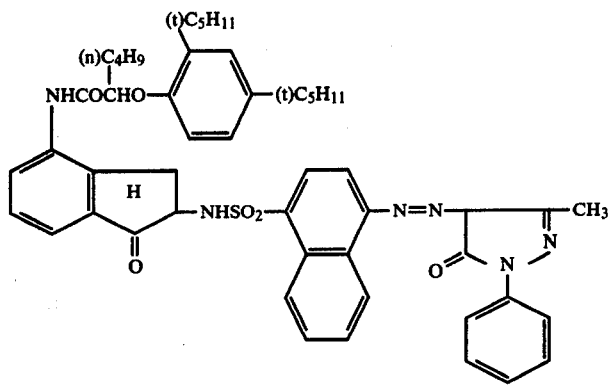 |
| (40) | 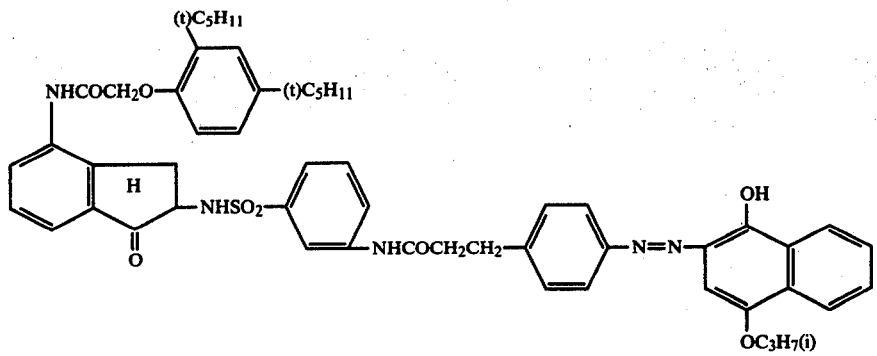 |
| (41) | 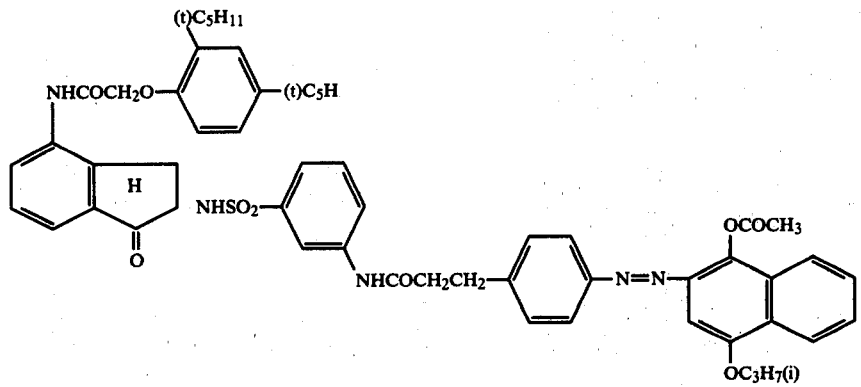 |
| (42) | 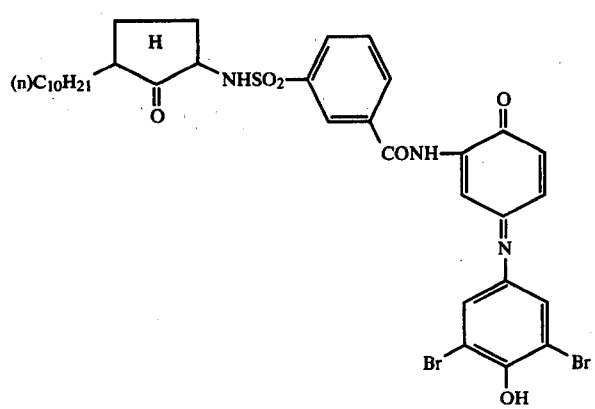 |
The compound of the above-mentioned general formula (I) used in this invention is prepared according to the synthetic procedures as described below.
The compound of the general formula (I) may be obtained by reacting the amine of the following general formula (II):

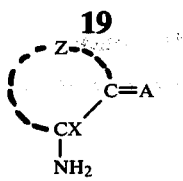

(wherein A, X and Z individually represent the same as described above), or a hydrochloride or sulfate of the amine, with D—(J)—SO₂X' (wherein D, J and n individually represent the same as described before and X' represents halogen) in the presence of a dehydrochlorinating agent such as an organic base like pyridine or triethylamine or an alkaline agent like caustic soda, caustic potash, sodium carbonate or sodium bicarbonate.

The compound of the above-mentioned general formula [I] may be also obtained in another process comprising reacting the amine of the above-mentioned general formula [II] or its hydrochloride or sulfate with a compound containing a nitro group or and a sulfonyl group such as nitrobenzenesulfonyl halide in the presence of such dehydrochlorinating agent as described above, converting an introduced nitro group into an amino group by the conventionally known process, preparing a diazonium salt with the conventionally known diazotizing agent such as sodium nitrite, isoamyl nitrite and then coupling the said diazonium salt with a suitable coupler.

Furthermore, the compound of the above-mentioned general formula [I] may be also obtained by reacting the amine of the above-mentioned general formula [II] or its hydrochloride or sulfate with such compound having a sulfonyl halide group at one terminal end thereof and a group containing active methine or active methylene at the other terminal end as e.g. [4-(m-chlorosulfonylphenyl)sulfonamide]-α-naphthol in the presence of a dehydrochlorinating agent and then coupling the resulting compound with a diazonium salt.

Preparation 1 - Compound (18)

(1) Preparation of 4-(2,5-di-tert-amylphenoxyacetamide)-2-nitroso-1-indanone 18 g of 4-(2,5-di-tert-amylphenoxyacetamido)-1-indanone was dissolved into 100 ml of benzene. While blowing hydrogen chloride thereinto, 4.2 g of isoamyl nitrite was added thereinto at a room temperature.

After stirring for three hours, crystals are collected by the filtration. The collected crystals are washed with benzene and then recrystallized from ethanol to obtain 13.5 g of the intended compound of m.p. 223° to 225° C.

(2) Preparation of 4-(2,5-di-tert-aminophenoxyacetamido)-2-amino-1-indanone hydrochloride 6.8 g of 4-(2,5-di-tert-aminophenoxyacetamido)-2-nitroso-1-indanone was dissolved into 140 ml of tetrahydrofuran. The resulted solution was added with 20 ml of ethanol and a small amount of Raney nickel and then reduced with hydrogen. After the termination of the reaction, hydrogen chloride was blown in and the catalyst was filtrated off. Then the filtrate was concentrated under vacuum. The crystals obtained were collected through a filter and washed with ethyl acetate to obtain 7.1 g of the intended compound of more than 300° C. m.p. (which began to discolor gradually into reddish violet color at a temperature above 160° C.).

(3) Preparation of Compound (18)

4.8 g of 4-(2,5-di-tert-amynophenoxyacetamido)-2-amino-1-indanone hydrochloride was added to 200 ml of pyridine under the nitrogen atmosphere and with ice cooling. Further, 4.0 g of 4-(3'-chloro-4'-hydroxyphenylazo)-1-benzenesulfonyl chloride was added thereinto and the reaction was carried out at a room temperature for two hours. After the termination of the reaction, the resultant mixture is poured into a diluted hydrochloric acid.

The precipitate formed was collected by filtration. The precipitate is refined by silica gel chromatography to obtain 4.2 g of the intended compound of m.p. 113° to 116° C.

Preparation 2 - Compound (32)

4.8 g of 4-(2,5-di-tert-aminophenoxyacetamide)-2-amino-1-indanone hydrochloride was added to 200 ml of pyridine under a nitrogen atmosphere and with ice cooling. Further, 5.4 g of 4-(3'-chlorosulfonylphenylazo)-1-phenyl-3-methyl-5-pyrazolone was added thereinto and the reaction was carried out with ice cooling for two hours. After the termination of the reaction, the resultant mixture was poured into a cool diluted hydrochloric acid. The precipitate was collected by filtration, water-washed and recrystallized from a mixed solvent of benzene and n-hexane to obtain 4.7 g of the intended compound of m.p. 123° to 126° C.

Preparation 3 - Compound (30)

4.8 g of 4-(2,5-di-tert-aminophenoxyacetamido)-2-amino-1-indanone hydrochloride was added to 200 ml of pyridine under a nitrogen atmosphere and with ice cooling. Further 4.8 g of 2-(3'-chlorosulfonylphenylazo)-4-propoxy-1-naphthol was added thereto and the reaction was carried out for two hours. After the termination of the reaction, the resultant mixture was poured into a cool diluted hydrochloric acid. The precipitate was recovered, water-washed and refined by silica gel chromatography to obtain the intended compound of m.p. 118°-121° C.

Thus, various kinds of the compounds of the above-mentioned general formula [I] may be prepared in the manner as described above. Among the compounds thus prepared, those illustrated as compounds (1) to (42) were subjected to the elementary analysis to give the respective results in the following table:

| Compound No. | Calculated | | | Found | | |
|---|---|---|---|---|---|---|
| | C % | H % | N % | C % | H % | N % |
| 1 | 64.90 | 7.46 | 8.41 | 64.67 | 7.34 | 8.35 |
| 2 | 64.30 | 7.26 | 8.65 | 64.02 | 7.31 | 8.76 |
| 3 | 62.86 | 5.82 | 7.58 | 62.94 | 5.73 | 7.59 |
| 4 | 63.42 | 6.03 | 7.40 | 63.46 | 5.95 | 7.78 |
| 5 | 70.86 | 7.50 | 5.90 | 71.02 | 7.41 | 5.75 |
| 6 | 60.04 | 6.59 | 8.08 | 60.18 | 6.69 | 8.25 |
| 7 | 67.50 | 7.99 | 6.05 | 67.71 | 8.13 | 6.31 |
| 8 | 65.72 | 8.27 | 9.58 | 65.69 | 8.22 | 9.83 |
| 9 | 68.93 | 8.43 | 6.89 | 68.91 | 8.53 | 6.82 |
| 10 | 61.58 | 6.64 | 7.69 | 61.33 | 6.63 | 7.68 |
| 11 | 68.84 | 7.18 | 7.30 | 68.57 | 7.01 | 7.35 |
| 12 | 60.89 | 6.13 | 10.65 | 61.10 | 6.30 | 10.52 |
| 13 | 68.84 | 7.36 | 10.03 | 68.98 | 7.30 | 9.89 |
| 14 | 69.95 | 8.16 | 5.97 | 70.13 | 8.31 | 6.04 |
| 15 | 65.73 | 7.29 | 8.21 | 66.00 | 7.46 | 8.19 |
| 16 | 57.73 | 6.40 | 7.21 | 57.88 | 6.18 | 7.29 |
| 17 | 60.90 | 6.50 | 12.91 | 60.97 | 6.34 | 13.19 |
| 18 | 64.05 | 5.93 | 7.66 | 64.21 | 5.93 | 7.64 |
| 19 | 63.01 | 7.44 | 10.89 | 63.24 | 7.57 | 11.15 |
| 20 | 54.02 | 5.13 | 11.61 | 54.20 | 5.03 | 11.86 |
| 21 | 64.89 | 6.48 | 12.27 | 64.77 | 6.50 | 12.23 |
| 22 | 65.21 | 6.24 | 12.38 | 64.07 | 6.43 | 12.41 |
| 23 | 65.25 | 5.95 | 10.87 | 65.24 | 6.07 | 10.94 |
| 24 | 66.07 | 7.96 | 7.90 | 66.21 | 7.91 | 8.07 |
| 25 | 64.59 | 6.19 | 10.76 | 64.36 | 6.08 | 10.99 |
| 26 | 65.30 | 6.63 | 12.03 | 65.47 | 6.58 | 12.20 |

-continued

| Compound No. | Calculated | | | Found | | |
|---|---|---|---|---|---|---|
| | C % | H % | N % | C % | H % | N % |
| 27 | 69.20 | 6.78 | 6.73 | 69.36 | 6.52 | 6.36 |
| 28 | 59.62 | 6.63 | 7.52 | 59.58 | 6.56 | 7.72 |
| 29 | 61.20 | 5.93 | 7.32 | 61.37 | 6.13 | 7.61 |
| 30 | 68.63 | 6.51 | 6.96 | 68.73 | 6.50 | 7.03 |
| 31 | 67.07 | 6.11 | 8.94 | 67.31 | 6.09 | 8.78 |
| 32 | 66.47 | 6.23 | 10.82 | 66.63 | 6.40 | 10.63 |
| 33 | 59.26 | 6.19 | 6.74 | 59.01 | 6.32 | 6.71 |
| 34 | 61.61 | 5.78 | 8.45 | 61.42 | 5.77 | 8.40 |
| 35 | 54.31 | 5.43 | 6.09 | 54.52 | 5.26 | 6.16 |
| 36 | 56.42 | 4.48 | 10.67 | 56.67 | 4.62 | 10.83 |
| 37 | 58.58 | 5.11 | 8.20 | 58.75 | 5.01 | 8.36 |
| 38 | 65.08 | 5.89 | 7.99 | 65.37 | 6.13 | 8.01 |
| 39 | 69.36 | 6.62 | 9.52 | 69.48 | 6.39 | 9.49 |
| 40 | 69.37 | 6.46 | 7.36 | 69.32 | 6.42 | 7.62 |
| 41 | 68.86 | 6.39 | 7.05 | 69.02 | 6.30 | 7.19 |
| 42 | 52.52 | 5.06 | 5.40 | 52.45 | 5.23 | 5.44 |

Further detailed description will be made below as to this invention.

The photographic element of this invention comprises at least a photosensitive element containing a silver halide emulsion layer and the compound of the above-mentioned general formula [I] as the DRR compound.

The silver halide emulsion is hydrophilic colloidal dispersion of silver bromide, silver iodide, silver chloride, silver iodobromide, silver chlorobromide, silver chloroiodide, silver chloroiodobromide or a mixture of these silver halides. The emulsion may include, in addition to conventionally known emulsions, those prepared in various methods; that is, such as the so-called conversion emulsions, the Lippmann's emulsions and the direct positive emulsions receiving beforehand fogs or latent images therein. The particle size, the contents or proportion of silver halides may be different according to the kinds of the photographic materials. As a hydrophilic protective colloid which is a dispersing medium for silver halide, various natural or synthetic colloid materials such as gelatin, gelatin derivative or polyvinyl alcohol may be used singly or in combination.

The silver halide may be chemically sensitized by using an activated gelatin; a sulfur sensitizer such as allylthiocarbamide, thiourea or cystine; a selen sensitizer; a noble metal sensitizer such as a gold sensitizer; or such sensitizer as ruthenium, rhodium or iridium sensitizer; singly or, if desired, in combination. Further, the silver halide emulsions may be optically sensitized, for example, with a cyanine dye or merocyanine dye and generally three kinds of silver halide emulsions respectively different in their sensitive wavelength ranges may be used to obtain a light sensitive color photographic material.

Further, the silver halide emulsion may be stabilized by triazoles, tetrazoles, imidazoles, azaindenes, quaternary benzothiazolium compounds, or zinc or cadmium compounds and may contain sensitizing compounds of the quaternary ammonium salt type or polyethyleneglycol type. The said emulsion may further contain the suitable gelatin plasticizer including e.g. glycerol, dihydroxyalkanes such as 1,5-pentandiol, esters of a ethylenebisglycolic acid, bis-ethoxydiethyleneglycolsuccinate, and acrylamide polymer type latex; the gelatin hardener including formaldehyde, halogen-substituted fatty acids such as mucobromic acid, such compounds as having an acid anhydride group, dicarboxylic chloride, biesters of methanesulfonate and sodium sulfite derivatives of dialdehyde in which aldehyde groups are separated by 2 or 3 carbon atoms; coating aids including saponin and sulfosuccinate; and various other photographic additives. Furthermore, if desired, various other conventionally known photographic additives such as fog inhibitors or ultraviolet absorbing agents may be contained in the emulsions.

In this invention as described above, various silver halide emulsions may be used and, in case of using a negative silver halide emulsion, a negative color diffusion transfer image may be obtained. A positive color diffusion transfer image may be obtained in various processes including such processes using a direct positive silver halide emulsion as disclosed in U.S. Pat. Nos. 3,227,552, 2,592,250, 2,005,837, 3,367,778 and 3,761,276, British Pat. No. 1,011,062, Japanese Patent Publication No. 17,184/66 and Japanese Laid-Open-to-Public Patent Publication No. 8,524/75, such processes using physical development as disclosed in British Pat. No. 904,364 and Japanese Laid-Open-to-Public Patent Publication No. 325/72 and processes using a combination of a negative silver halide emulsion layer and an adjacent layer, the emulsion layer containing a compound which releases a development inhibitor by reacting with an oxidation product of a developing agent while the adjacent layer containing a color image forming material and a fogged emulsion as disclosed in Japanese Laid-Open-to-Public Patent Publication No. 21,778/68 and U.S. Pat. Nos. 3,227,554 and 3,632,345.

While a positive color diffusion transfer image may be obtained in various processes. The preferred example of such process may be a process using a direct positive silver halide emulsion. The direct positive silver halide emulsion may include, for example, such silver halide emulsion that is previously exposed or chemically processed so as to be developed over the whole but is imagewise undeveloped when imagewise exposed thereafter.

As another direct positive silver halide emulsion, there may be a direct positive silver halide emulsion having sensitive centers within its silver halide particles. In this invention, the direct positive silver halide emulsion of the latter type is preferable. In this direct positive silver halide emulsion, a latent image is formed mainly within silver halide particles by imagewise exposure and a positive silver image is formed by the surface development as fogging the silver halide emulsion. There are various processes for such development, including such processes using the so-called air fog developing agent as disclosed in West German Pat. No. 850,383 and U.S. Pat. No. 2,497,875, such processes using a flash exposure over the whole at the time of development as disclosed in West German Pat. No. 854,888, U.S. Pat. No. 2,592,298 and British Pat. Nos. 1,150,553, 1,195,838 and 1,187,029, and processes carrying out development in the presence of a fogging agent. The fogging agent used in this case may be hydrazine type compounds and N-substituted quaternary ammonium salts, which may be used singly or in combination. Such fogging agent are disclosed in U.S. Pat. Nos. 2,588,982, 3,227,552, 3,615,615, 3,719,494, 5,734,738 and 3,718,470.

In the above-mentioned processes, an amount of a fogging agent may be used in a wide range according to intended purpose. Generally, the amount may be 0.1 to 2.0 g based on one liter of a developing solution when said agent is added into the developing solution and it may be 0.01 to 0.2 g based on one square meter when the agent is added into a photographic element.

In this invention, a photographic element comprises a combination of the above-mentioned silver halide emulsion with the compound of the above-mentioned general formula [I] as the DRR compound. By using one or two sets of combinations of silver halide emulsions and the DRR compounds, a singly-color or two-color pseudo color photographic image may be obtained. For a color diffusion transfer process according to a multicolor subtraction process, blue, green and red light sensitive silver halide emulsions may be used respectively in combination with yellow, magenta and cyan DRR compounds.

A preferable example of the multi-layer construction comprises successively the blue, green and red light sensitive emulsion layers from the light exposure side, wherein a yellow filter layer may be disposed between the blue light sensitive emulsion and the green light sensitive emulsion. In an certain way of combination of a light sensitive silver halide emulsion and the DRR compound, they may be added individually into different adjacent layers and, in case of using a shorter wavelength shift type DRR compound as the compound of the above-mentioned general formula [I], it is advantageous that the DRR compound may be added into a silver halide emulsion layer because the compound does not work to reduce sensitivity of the emulsion.

Further, it may be possible to use more than two kinds of silver halide emulsions and more than two kinds of DRR compounds by coating them on one layer according to such mixed bucket process as disclosed in U.S. Pat. Nos. 2,800,458 and 3,466,662.

The DRR compound used in this invention is dissolved into an organic solvent in as small an amount as possible and dispersed into a hydrophilic protective colloid, e.g. gelatin polyvinyl alcohol, as a support of a silver halide emulsion layer or its adjacent layer in an photographic element. As said organic solvent, a high boiling solvent, a low boiling solvent which may be removed from a dispersed material by distillation, or an organic solvent easily soluble into water may be used singly or in combination.

As the particularly useful high boiling solvent, there may be N-n-butylacetanilide, diethyllaurylamide, dibutyl phthalate, tricresyl phosphate and the like. As the useful low boiling solvent, there may be ethyl acetate, methyl acetate, cyclohexanone and the like. These low boiling solvents may be removed away at the time of drying after coating or they may be removed before coating in such process as disclosed in U.S. Pat. No. 2,801,171.

As the organic solvent easily miscible with water, there may be used 2-methoxyethanol, dimethylformamide and the like.

Instead of the high boiling solvent or as an additive to the high boiling solvent, there may be used various lipophilic polymers. As such lipophilic polymer, polyvinylacetate, ester polyacrylate and the esters of polyhydric alcohol and polybasic acid may be used.

Such processes as disclosed in Japanese Patent Publication Nos. 13,837/68 and 32,131/73, U.S. Pat. No. 3,832,173 and Japanese Laid-Open-to-Public Patent Publication No. 17,637/75 are useful for dispersing a color image forming material in this invention.

The color image forming material having a water soluble group as a carboxyl group or a sulfo group, may be dissolved into an alkaline aqueous solution and dispersed into a hydrophilic protective colloid, followed by neutralization if desired.

While an amount of the DRR compound used in this invention may vary in a wide range according to compounds to be used or desired results, it is generally preferable to use about 0.5 to about 1.0 weight % in a water soluble organic colloid coating solution.

In case of carrying out a multicolor diffusion transfer process, it is advantageous to use an inter layer in a photographic element. An inter layer comprises gelatin, polyacrylamide, calcium alginate, partly hydrolized polyvinylacetate, hydroxypropyl cellulose, and the like hydrophilic polymer and in addition thereto such polymer, formed from a latex of a hydrophilic polymer and a hydrophobic polymer, as disclosed in U.S. Pat. No. 3,625,685.

Such compounds as disclosed in U.S. Pat. Nos. 3,384,483, 3,421,892, 3,427,158, 3,121,011, 3,043,692, 3,069,263, 3,615,422, 3,625,685, 3,756,816 and 3,069,264 also may be used for the inter layer.

In order to inhibit the occurrence of undesirable color mixture due to diffusion of the oxidation product of a developing agent into other layers in a photographic element, it is preferable to add a coupler, an amidorazone compound as disclosed in Japanese Laid-Open-to-Public Patent Publication No. 15,532/73, a hydrazone compound as disclosed in West German Patent 2,123,268, a nondiffusible hydroquinone derivative or the like into an inter layer or a layer between a silver halide emulsion layer and an image receiving layer. A non-diffusible hydroquinone derivative also may be added into a silver halide emulsion.

As a support for the photographic element of this invention, there may be various natural or synthetic polymers such as paper, glass, cellulose nitrate, cellulose acetate, polyvinylacetal, polycarbonate, polystyrene, polyethylenetelephthalate, polypropylene polyethylene or the like. The support may be either transparent or opaque depending on the purpose.

Such vapor-permeable support or oxygen-barrier support as disclosed in U.S. Pat. No. 3,573,044 may be used advantageously. Further, in case of using a transparent support, it is preferable that the support is colored to such an extent as not to disturb the light exposure and the visual observation of formed images but as to inhibit the fogging of the emulsion at the time of processing due to piping light coming from the side portions of the support.

In this invention, the above-mentioned photographic element is imagewise exposed and developed with the below-mentioned alkaline processing solution in the presence of a developing agent. By this development, the compound of the above-mentioned general formula [I] and other DRR compounds incorporated into a photographic element release diffusible dyes or their precursors imagewise. In this case, when D in the above-mentioned general formula [I] is a dye moiety, the diffusible dyes are released by development and when D is a dye precursor moiety the diffusible dyes or their precursors are released by development. The diffusion transfer of these diffusible dyes to an image receiving layer, which is superposed on a photosensitive element (which is explained later in more detail) at least during development, takes place so as to have said dyes fixed onto the image receiving layer, thereby to form color images.

The diffusible color precursors are transformed into dyes in such processes as above described to form color images in an image receiving layer.

It is preferable that the image receiving layer contains a mordant. As the mordant suitable for the receiving layer there may be used any compounds having a preferable mordanting effect on such diffusible dyes or precursors thereof as subjected to the diffusion transfer and the useful mordant includes such as poly-4-vinylpyridine, poly-4-vinyl-N-benzylpyridinium-p-toluenesulfonate, setyltrimethyl ammonium bromide and the like. Such mordants as disclosed in U.S. Pat. No. 2,882,156, Belgian Pat. No. 729,202, U.S. Pat. Nos. 3,448,706, 3,859,096, 3,788,855, 3,227,148, 3,271,147, 3,709,690, 3,625,694, 3,770,439, and 3,756,814 and Japanese Laid-Open-to-Public Patent Publication No. 61,228/75 may be advantageously used in this invention.

The above mordants are usually used with various kinds of dispersing agents such as gelatin, polyvinylalcohol, polyvinylpyrrolidone or wholelly or partially hydrolyzed cellulose ester. Further, the image receiving layer may not comprise a mordant if a binder of the layer has a sufficient mordanting effect, said binder being such as poly-N-methyl-2-vinylpyridine, N-methoxy-methyl-polyhexamethylene adipamide, a copolymer of vinylalcohol and N-vinylpyrrolidone, a mixture of polyvinylalcohol and poly-n-vinylpyrrolidone, a partially hydrolized polyvinylacetate, acetylcellulose, gelatin, polyvinylalcohol, and a guanylhydrazone derivative of acylstyrene copolymer.

As the special example, a mordant may be contained in an alkaline processing solution as disclosed in Japanese Laid-Open-to-Public Publication No. 47,626/75.

The image receiving layer may contain further various kinds of additives conventionally known in the photographic arts, such as an ultraviolet absorbing agent or a fluorescent whitening agent.

After carrying out the diffusion transfer of the diffusible dyes or their precursors to the image receiving layer by applying an alkaline processing solution substantially to accomplish the formation of dye images, it is necessary to reduce pH within a film unit to about neutrality not only to promote stability of the dye images but also substantially to stop any further image formation for preventing such discoloration or contamination of the images as occuring at a higher pH. It is advantageous for this purpose to use a neutralizing layer containing such material as being capable sufficiently to reduce pH. As the material useful in this invention there may be such polymer acids or partial esters or acid anhydrides thereof as disclosed in U.S. Pat. No. 3,362,819, such higher fatty acids as disclosed in U.S. Pat. No. 2,983,606 and such solid acid metallic salts as disclosed in U.S. Pat. No. 2,584,030.

Such microcapsulation as disclosed in U.S. Pat. No. 3,576,625 may be also helpful for the present invention.

Furthermore, it is preferable to use a timing layer in order to control the pH reducing rate. As a material used for the said layer, there may be used such as gelatin, hydroxypropyl cellulose, partially hydrolyzed polyvinyl acetacrylate latex polyacrylamide, acetyl cellulose, polyvinyl alcohol, partially acetalized polyvinyl alcohol and the like.

A combination of the neutralizing layer and the timing layer can be positioned on a support of a photosensitive element, an image receiving element, or a cover sheet (which are explained later in detail) directly or through other layers. In this case, the timing layer is placed between the neutralizing layer and a space in which an alkaline processing solution is spread.

The alkaline processing solution used in this invention contains such components as necessary to develop a silver halide emulsion and to form diffusible dyes and has a high alkalinity, generally higher than pH 10.

The alkaline processing solution used in this invention contains hydroxide of an alkaline earth metal, (e.g. sodium hydroxide, potassium hydroxide, calcium hydroxide or lithium hydroxide), sodium carbonate or diethylamine.

It is desirable that the alkaline processing solution contains a silver halide developing agent.

The silver halide developing agent used in this invention may include e.g. hydroquinone, 1-phenyl-3-pyrazolidone, 1-phenyl-4,4-dimethyl-3-pyrazolidone, 1-phenyl-4-methyl-4-hydroxymethyl-3-pyrazolidone, ascorbic acid, aminophenol, N-methylaminophenol, N,N-diethyl-p-phenylenediamine and 3-methoxy-N-ethyl-N-ethoxy-p-phenylenediamine.

While there may be used such a variety of silver halide developing agents as described above, a black-white silver halide developing agent is particularly preferable in order to reduce the contamination of a dye image formed. While the above-mentioned silver halide developing agent is generally contained into the alkaline processing solution, the agents may also be contained beforehand into a photosensitive element. Further, the agent may be contained both into the alkaline processing solution and into the photosensitive element. In case of incorporating beforehand the agent into the photosensitive element, the agent may also be contained in the form of precursors.

It is also preferable to add to an alkaline processing solution such a thickner as hydroxyethyl cellulose, sodium carboxymethyl cellulose or the like.

Further into an alkaline processing solution, there may be added the compounds suitable for the improvement of photographic properties, such as sodium sulfite, potassium iodide, triazole type compounds, mercapto type compounds or color balancing compounds.

While the above alkaline processing solution may be applied in various forms to the photosensitive element, the solution may preferably be applied to the exposed photosensitive element in such manner that the solution is held in a rupturable container and, after the exposure of the photographic element, the container is ruptured by means of a pressure member attached to the inner part of a camera and/or a film unit cartridge after the exposure of the photosensitive element, thereby to apply the solution to the photosensitive element.

As the rupturable container, there may be used such containers as disclosed in U.S. Pat. Nos. 2,543,181, 2,643,886, 2,723,051, 3,056,492, and 3,152,515.

The film unit as a typical example of photographic elements of the invention comprises a photosensitive element, an image receiving element and a rupturable container holding an alkaline processing solution. In said unit, the photosensitive element and the image receiving element may be situated seperated from each other before the exposure or the both may be combined as one body, and after processing, the photographic element and the image receiving element may be kept in one body or both may be stripped off.

In case of using the film unit in such process that the photosensitive element and the image receiving layer are situated separated from each other before the exposure or both are stripped off after processing, it is necessary to form an image receiving layer on a different support from that of the photosensitive element in order to obtain the image receiving element.

As the support for the image receiving layer there may be used those as mentioned before as to photographic element and the support may be either transparent or opaque.

Further, the image receiving layer may be formed on the same support of the photosensitive element to obtain a combination of the photosensitive element and the image receiving element. In this case, it is preferable to use the so-called cover sheet in combination with both the elements so that the alkaline processing solution is spread between the cover sheet and the photosensitive element. This cover sheet comprises a support which may be those as already mentioned for the photographic element. It is good to form, as a background for the formed images, a light reflecting layer of high whiteness on the side opposite to the observing side.

While the position of the light reflecting layer is not particularly limited, it is good to form the layer between the photosensitive element and the image receiving element in the case that the photographic element and the image receiving layer are not stripped off after processing. The light reflecting layer may be formed beforehand or a light reflecting agent may be present in an alkaline processing solution which is formed as a light reflecting layer at the time of processing. As the light reflecting agent, there may be used such as titanium dioxide, zinc oxide, barium sulfate, flake silver, alumina, barium stearate and zirconium oxide, singly or in admixture of two or more kinds thereof. In case of forming a layer beforehand, said agent may be dispersed into any of binders permeable into an alkaline solution, such as gelatine or polyvinylalcohol.

As a process for forming a light reflecting layer, there may be used such as disclosed in Japanese Laid-Open-to-Public Patent Publication Nos. 486/71 and 477/72.

The above light reflecting layer may be added with such whitening agent as stilbene or coumarin. In case of developing the silver halide emulsion outside a camera after the exposure, it is desirable to form an opacifying agent layer in order to protect the silver halide emulsion from additional light exposure. The opacifying agent containing layer may be either formed beforehand or at the time of processing.

As the opacifying agent, there may be added carbon black or such indicator dyes as disclosed in Japanese Laid-Open-to-Public Patent Publication Nos. 26/72, 27/72 and 28/72. It may also be advantageous to use such desensitizing agents as disclosed in U.S. Pat. No. 3,579,333.

The above-mentioned light reflecting agent layer and the above opacifying agent layer may be formed either as one same layer or as the respectively individual layers adjacent with each other.

As the layer arrangement of the film unit in this invention, there may be used such many kinds as disclosed in U.S. Pat. Nos. 3,415,644, 3,415,645, 3,415,646, 3,473,925, 3,573,042, 3,573,043, 3,594,164, 3,594,165, 3,615,421, 3,576,626, 3,658,524, 3,635,707, 3,672,890, 3,730,718, 3,701,656 and 3,689,262; Japanese Laid-Open-to-Public Patent Publication No. 6,337/75; and Belgian Pat. Nos. 757,959 and 757,960.

In the various film unit as described above, such a filter dye as suitable to improve some photographic properties, if desired, may be added into a layer between a silver halide emulsion layer and the exposure surface of the unit. As the filter dye, there may be used such dye as is stable at an ordinary pH but may be made colorless due to decomposition or the like when brought into contact with the alkaline processing solution.

After the formation of the dye images in the image receiving layer, there remain, in the photographic element, silver images and images of the DRR compound reversally corresponding to the diffusion transfer images. These remaining silver and silver halide can be removed in a bleaching bath and then a fixing bath or in a bleaching-fixing bath and, if desired, further processed to transform the dye precursor moiety into dyes, thereby to obtain the dye images reversed from the dye images formed in the image receiving layer.

BRIEF DESCRIPTION OF THE PREFERRED EMBODIMENTS

The present invention is illustrated below with reference to the examples, but the invention is not intended to be limited thereto.

EXAMPLE 1

A monocolor photosensitive element was prepared by successively forming the following layers on the another side of a transparent polyethyleneterephthalate film support having the thickness of about 110 $\mu$m:

(1) A layer having the dry thickness of 1.4 $\mu$m, containing 10.0 mg/100 cm$^2$ of the yellow DRR compound of compound (18), 5.0 mg/100 cm$^2$ of tricresyl phosphate and 13.6 mg/100 cm$^2$ of gelatin, (2) A layer having the dry thickness of 1.2 $\mu$m, comprising a blue light sensitive, interval latent image type silver iodobromide emulsion containing 14.0 mg/100 cm$^2$ of silver, 1.0 mg/100 cm$^2$ of potassium 2-octadecylhydroquinone-5-sulfobinate, 0.13 mg/100 cm$^2$ of formyl-4'-methylphenylhydrazide and 12.3 mg/100 cm$^2$ of gelatin, and (3) A protective layer having the dry thickness of 0.9 $\mu$m, comprising 10.0 mg/100 cm$^2$ of gelatin.

In the above-mentioned photosensitive element, compound (18) was dispersed in the following manner:

Compound (18) was dissolved into ethyl acetate and tricresyl phosphate, and the resulting solution was emulsified and dispersed into an aqueous gelatin solution containing Alkanol XC (Product of E. I. du Pont de Nemours & Co.) as a surfactant.

Then, an image receiving element was prepared by successively forming the following layers on a transparent polyethyleneterephthalate film support having the thickness of about 100 $\mu$m:

(1) A neutralizing layer having the thickness of 25.0 $\mu$m comprising 24.8 mg/100 cm$^2$ of polyacrylic acid, (2) A timing layer having the dry thickness 3.0 $\mu$m, comprising 5.0 mg/100 cm$^2$ of cellulose acetate, and (3) An image receiving layer having the dry thickness of about 2.0 $\mu$m, comprising 22.0 mg/100 cm$^2$ of a coplymer of styrene with N-benzyl-N,N-dimethyl-N-(3-maleimidepropyl)ammonium chloride at the ratio of 1:1 and 22.0 mg/100 cm$^2$ of gelatin.

The prepared monocolor photosensitive element was exposed through the whole 30-step silver wedge with each density difference of 0.15 and then superposed on the abovementioned image receiving element, while a rupturable container containing 1.0 ml of the below-mentioned alkaline processing solution is attached therebetween, thereby to prepare a film unit as a photographic element.

Then, the said film unit was passed through one set of juxtaposed pressing rolls having the opening of about 80 μm to burst the above-mentioned rupturable container and to spread its contents between the photosensitive element and the image receiving element.

The composition of the above-mentioned alkaline processing solution used was as follows:

| | |
|---|---|
| Potassium hydroxide | 28.0 g |
| Sodium sulfite | 1.0 g |
| 1-Phenyl-3-pyrazolidone | 4.0 g |
| 5-Methylbenzotriazole | 14.0 g |
| Titanium dioxide | 500.0 g |
| Carboxycellulose sodium salt | 50.0 g |
| Benzylalcohol | 5.0 ml |
| Distilled Water | To make total of 1000.0 ml |

After about 8 to 10 minutes, the dye image was observed through the transparent support of the image receiving element.

The reflective density of the obtained dye images was measured through the blue (λ max=436 mm) filter by Sakura Photoelectric Densitometer, to give the following results:

| | |
|---|---|
| D max (Maximum transfer density) | 1.97 |
| D min (Minimum transfer density) | 0.25 |

EXAMPLE 2

On the supprt used in Example 1, the following layers were successively formed in the same manner in Example 1 to prepare a monochromatic photosensitive element:

(1) A layer having the dry thickness of about 1.1 μm, comprising a green light sensitive silver iodobromide emulsion containing 11.3 mg/100 cm$^2$ of silver and 12.2 mg/100 cm$^2$ of gelatin, (2) A layer having the dry thickness of about 1.5 μm, comprising 8.0 mg/100 cm$^2$ of compound (30) as a magenta DRR compound and 14.0 mg/100 cm$^2$ of gelatin, and (3) A protective layer having the dry thickness of about 0.9 μm, comprising 10.0 mg/100 cm$^2$ of non-modified gelatin.

In the above-mentioned photosensitive element, compound (30) was dispersed in the following manner:

Compound (30) was dissolved into acetone and the resulting solution is filtrated to remove the insolubles in acetone. The obtained filtrate was poured into 125 ml of water to precipitate the above-mentioned compound. This precipitate was collected by filtration and washed with water. An aqueous slurry containing 10% per weight of Alkanol XC was prepared, dispersed by the supersonic wave homogenizer and then dispersed into gelatin.

Then, an image receiving layer was prepared by successively forming the layers of the image receiving element in Example 1 on a cellulose acetate-coated baryta paper support.

The photographic element was exposed as in Example 1 and the processing was carried out as in Example 1 by using the below-described alkaline processing solution and the above-mentioned image receiving element.

Composition of the alkaline processing solution:

| | |
|---|---|
| Potassium hydroxide | 30.0 mg |
| Sodium sulfite | 1.0 mg |
| 1-Phenyl-3-pyrazolidone | 4.0 mg |
| 5-Methylbenzotriazole | 0.8 g |
| Potassium bromide | 0.1 g |
| Carboxymethylcellulose sodium salt | 5.0 g |
| Distilled water | To make total of 1,000 ml |

After two minutes the image receiving element was stripped off from the photosensitive element and dried. The reflective density of the obtained transfer image was measured through a green filter.

| | |
|---|---|
| D max | 1.92 |
| D min | 0.21 |

EXAMPLE 3

On a transparent polyethyleneterephthalate film support having the thickness of 100 μm, the following layers were formed successively to prepare a multilayer multicolor photosensitive element and image receiving element.

(1) An image receiving layer having the dry thickness of 1.5–2.0 μm, comprising 22 mg/100 cm$^2$ of a copolymer of styrene with N-vinylbenzyl-N,N,N-trihexyl ammonium chloride at the ratio of 1:1 and 22 mg/100 cm$^2$ of gelatin, (2) A light reflecting layer having the dry thickness of 6–7 μm, comprising 220 mg/100 cm$^2$ of titanium dioxide and 22 mg/100 cm$^2$ of gelatine, (3) A black opaque layer having the dry thickness of 4 μm, comprising 20.5 mg/100 cm$^2$ of carbon black and 42.0 mg/100 cm$^2$ of gelatin, (4) A layer having the dry thickness of 1.1 μm, comprising 8.0 mg/100 cm$^2$ of the cyan DRR compound of compound (37), 4.0 mg/100 cm$^2$ of tricresyl phosphate and 11.0 mg/100 cm$^2$ of gelatin, (5) A layer having the dry thickness of 1.2 μm, comprising a red light sensitive latent image type silver iodobromide emulsion containing 14.0 mg/100 cm$^2$ of silver, 0.7 mg/100 cm$^2$ of potassium 2-octadecylhydroquinone-5-sulfonate, 0.14 mg/100 cm$^2$ of formyl-4'-methylphenylhydrazide and 12.0 mg/100 cm$^2$ of gelatin, (6) An inter layer having the dry thickness of about 1.0 μm, comprising 6.0 mg/100 cm$^2$ of 2,5-di-tert-octylhydroquinone, 6.0 mg/100 cm$^2$ of di-n-butyl phthalate and 12.0 mg/100 cm$^2$ of gelatin, (7) A layer having the dry thickness of 1.3 μm, comprising 10.0 mg/100 cm$^2$ of compound (40) as a magenta DRR compound, 5.0 mg/100 cm$^2$ of tricresyl phosphate and 13.1 mg/100 cm$^2$ of gelatin, (8) A layer having the dry thickness of 1.2 μm, comprising a green light sensitive latent image type silver iodobromide emulsion containing 14.2 mg/100 cm$^2$ of silver, 1.0 mg/100 cm$^2$ of potassium 2-octadecylhydroquinone-5-sulfonate, 0.13 mg/100 cm$^2$ of formyl-4'-methylphenylhydrazide and 12.0 mg/100 cm$^2$ of gelatin, (9) An inter layer having the dry thickness of about 1.0 μm, comprising 6.0 mg/100 cm$^2$ of 2,5-di-tert-octyl-hydroquinone, 6.0 mg/100 cm$^2$ of di-n-butyl phthalate, 3.5 mg/100 cm$^2$ of yellow colloid silver and 12.0 mg/100 cm$^2$ of gelatin,

(10) A layer having the dry thickness of 1.6 μm, comprising 13.0 mg/100 cm² of compound (32) as a yellow DRR compound, 6.0 mg/100 cm² of tricresyl phosphate and 15.8 mg/100 cm² of gelatin,

(11) A layer having the dry thickness of 1.2 μm, comprising a blue light sensitive latent image type silver iodobromide emulsion containing 14.5 mg/100 cm² of silver, 0.7 mg/100 cm² of potassium 2-octadecylhydroquinone-5-sulfonate, 0.14 mg/100 cm² of formyl-4'-methylphenylhydrazide and 12.0 mg/100 cm² of gelatin, and

(12) A protective layer having the dry thickness of about 0.9 μm, comprising 10.0 mg/100 cm² of gelatin.

Then, a cover sheet was prepared by successively forming the following layers on a transparent polyethyleneterephthalate film support having the thickness of 100 μm:

(1) A neutralizing layer having the dry thickness of 25.0 μm, comprising 25.1 mg/100 cm² of polyacrylic acid, and (2) A timing layer having the dry thickness of 3.0 μm, comprising 5.5 mg/100 cm² of cellulose acetate.

The multilayer multicolor photosensitive element and image receiving element thus obtained was exposed respectively through yellow, magenta and cyan filters to the blue, green and red lights and then superposed on the cover sheet, while a rupturable container containing 1.0 ml of the below-mentioned alkaline processing solution is attached therebetween, thereby to prepare a film unit. This film unit was passed through one set of juxtaposed pressing rollers having the opening of 80 μm to burst the above-mentioned burstible container and to spread its contents between the photosensitive element and the cover sheet.

The composition of an alkaline processing solution used was as follows:

| | |
|---|---|
| Potassium hydroxide | 56 g |
| Sodium sulfite | 2.0 g |
| 1-Phenyl-3-pyrazolidone | 8.0 g |
| 5-Methylbenzotriazole | 2.8 g |
| Carbon black (MA-ICO, a product of Mitsubishi Chemical Industries, Ltd.) | 100.0 g |
| Carboxymethylcellulose sodium salt | 50.0 g |
| Benzylalcohol | 10.0 ml |
| Distilled Water | To make the total of 1000.0 ml |

After about 8–10 minutes, preferable dye images was observed through the transparent support of the above-mentioned photosensitive element and image receiving element.

What is claimed is:

1. A color diffusion transfer photographic element comprising a photosensitive element having a support and a silver halide photosensitive layer wherein said photographic element is processed with an alkaline processing solution after imagewise exposure to obtain a dye image, said photographic element comprising a compound represented by the formula

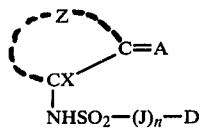

wherein A represents oxygen or a group =NR (in which R represents hydroxyl or an amino group); X represents hydrogen or halogen; Z represents a group of nonmetallic atoms necessary to form a first ring and being a 5 to 7-membered non-aromatic hydrocarbon ring which may be fused with a second ring, at least one of said first ring and said second ring having one or more substituents wherein at least one of said substituents is a ballast group which renders said compound nondiffusible during processing with said solution; J represents a divalent group; D represents a dye moiety or a dye precursor moiety; and n represents zero or 1.

2. The photographic element according to claim 1 wherein A is oxygen.

3. The photographic element according to claim 1 wherein A is the =NR group.

4. The photographic element according to claim 1 wherein said second ring is aromatic.

5. The photographic element according to claim 4 wherein said second ring is benzene.

6. The photographic element according to claim 1 wherein said first ring is not fused with said second ring.

7. A color diffusion transfer photographic element comprising a photosensitive element and an image receiving element wherein said photosensitive element contains a first support and a silver halide photosensitive layer and said photographic element is processed with an alkaline processing solution after imagewise exposure to obtain a dye image, said photosensitive element containing a compound represented by the formula

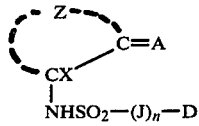

wherein A represents oxygen or a group =NR (in which R represents hydroxyl or an amino group); X represents hydrogen or halogen; Z represents a group of nonmetallic atoms necessary to form a first ring and being a 5 to 7-membered non-aromatic hydrocarbon ring which may be fused with a second ring, at least one of said first and said second rings having one or more substituents wherein at least one of said substituents is a ballast group which renders said compound nondiffusible during processing with said solution; J represents a divalent group; D represents a dye moiety or a dye precursor moiety; and n represents zero or 1.

8. The photographic element according to claim 7 wherein said compound is in a layer between said first support and said photosensitive layer.

9. The photographic element according to claim 8 wherein the image receiving element comprises a second support having thereon a neutralizing layer, said neutralizing layer having thereon a timing layer, and said timing layer having thereon an image receiving layer.

10. The photographic element according to claim 9 wherein said second support is transparent.

11. The photographic element according to claim 9 wherein said first support is opaque.

12. The photographic element according to claim 11 wherein the alkaline processing solution contains titanium dioxide.

13. A color diffusion transfer photographic element comprising a first support having thereon an image receiving layer, said image receiving layer having thereon a silver halide photosensitive layer which contains a compound of the formula

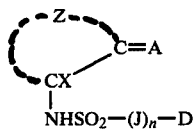

wherein A represents oxygen or a group =NR (in which R represents hydroxyl or an amino group); X represents hydrogen or halogen; Z represents a group of nonmetallic atoms necessary to form a first ring and being a 5 to 7-membered non-aromatic hydrocarbon ring which may be fused with a second ring, at least one of said first and said second rings having one or more substituents wherein at least one of said substituents is a ballast group which renders said compound nondiffusible during processing with said solution; J represents a divalent group; D represents a dye moiety or a dye precursor moiety; and n represents zero or 1.

14. A color diffusion transfer photographic element comprising, in order, a first support, an image receiving layer, and a pair of layers comprising a compound containing layer and a silver halide photosensitive layer, said compound containing layer containing a compound of the formula

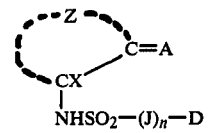

wherein A represents oxygen or a group =NR (in which R represents hydroxyl or an amino group); X represents hydrogen or halogen; Z represents a group of non-metallic atoms necessary to form a first ring and being a 5 to 7-membered non-aromatic hydrocarbon ring which may be fused with a second ring, at least one of said first and second rings having one or more substituents wherein at least one of said substituents is a ballast group which renders said compound nondiffusible during processing with an aqueous alkaline solution; J represents a divalent group; D represents a dye moiety or a dye precursor moiety; and n represents zero or 1.

15. The photographic element according to claim 14 further comprising a reflecting layer containing titanium dioxide between said image receiving layer and said compound containing layer.

16. The photographic element according to claim 15 wherein said photographic element further comprises a cover sheet comprising a second support having thereon a neutralizing layer, said neutralizing layer having thereon a timing layer, whereby said layers are positioned between said first and said second supports.

17. The photographic element according to claim 16 wherein said first, and said second supports are transparent.

18. The photographic element according to claim 17 wherein said photographic element further comprises a carbon black containing layer between said reflecting layer and said compound containing layer.

* * * * *